United States Patent
Cho et al.

(10) Patent No.: US 11,664,535 B2
(45) Date of Patent: May 30, 2023

(54) ELECTROLYTE FOR LITHIUM SECONDARY BATTERY AND LITHIUM SECONDARY BATTERY INCLUDING THE SAME

(71) Applicant: SK ON CO., LTD., Seoul (KR)

(72) Inventors: In Haeng Cho, Daejeon (KR); Dong Gun Lee, Daejeon (KR); Joo Hyun Lee, Daejeon (KR); Sung Jin Kim, Daejeon (KR)

(73) Assignee: SK ON CO., LTD., Seoul (KR)

(*) Notice: Subject to any disclaimer, the term of this patent is extended or adjusted under 35 U.S.C. 154(b) by 205 days.

(21) Appl. No.: 17/220,114

(22) Filed: Apr. 1, 2021

(65) Prior Publication Data

US 2021/0313622 A1    Oct. 7, 2021

(30) Foreign Application Priority Data

Apr. 3, 2020 (KR) .................. 10-2020-0040945

(51) Int. Cl.
*H01M 10/0567* (2010.01)
*C07C 309/67* (2006.01)
*C07F 9/06* (2006.01)
*H01M 10/0525* (2010.01)
*H01M 10/0568* (2010.01)
*H01M 10/0569* (2010.01)

(52) U.S. Cl.
CPC ....... *H01M 10/0567* (2013.01); *C07C 309/67* (2013.01); *C07F 9/062* (2013.01); *H01M 10/0525* (2013.01); *H01M 10/0568* (2013.01); *H01M 10/0569* (2013.01); H01M 2300/0025 (2013.01)

(58) Field of Classification Search
CPC ........ C07C 309/67; C07F 9/062; C07F 9/146; H01M 10/0525; H01M 10/0567; H01M 10/0568; H01M 10/0569; H01M 2300/0025; Y02E 60/10
See application file for complete search history.

(56) References Cited

U.S. PATENT DOCUMENTS

| | | |
|---|---|---|
| 2011/0136019 A1 | 6/2011 | Amiruddin et al. |
| 2017/0025706 A1 | 1/2017 | Dahn et al. |

FOREIGN PATENT DOCUMENTS

| | | |
|---|---|---|
| JP | 200841296 A | 2/2008 |
| JP | 2014146517 A | 8/2014 |
| JP | 2014160575 A | 9/2014 |
| JP | 201733838 A | 2/2017 |
| KR | 1020120101499 A | 9/2012 |
| KR | 1020150089712 A | 8/2015 |
| KR | 1020160129584 A | 11/2016 |
| KR | 1020200104650 A | 9/2020 |
| WO | 2015153716 A1 | 10/2015 |

*Primary Examiner* — Victoria H Lynch
(74) *Attorney, Agent, or Firm* — The Webb Law Firm

(57) ABSTRACT

An electrolyte for a lithium secondary battery according to exemplary embodiments of the present inventing includes an organic solvent, a lithium salt, a first additive represented by a predetermined chemical formula, and a second additive represented by a predetermined chemical formula. A protective film is formed by the additives to suppress an expansion of a lithium secondary battery and improve storage property at high temperature.

14 Claims, 1 Drawing Sheet

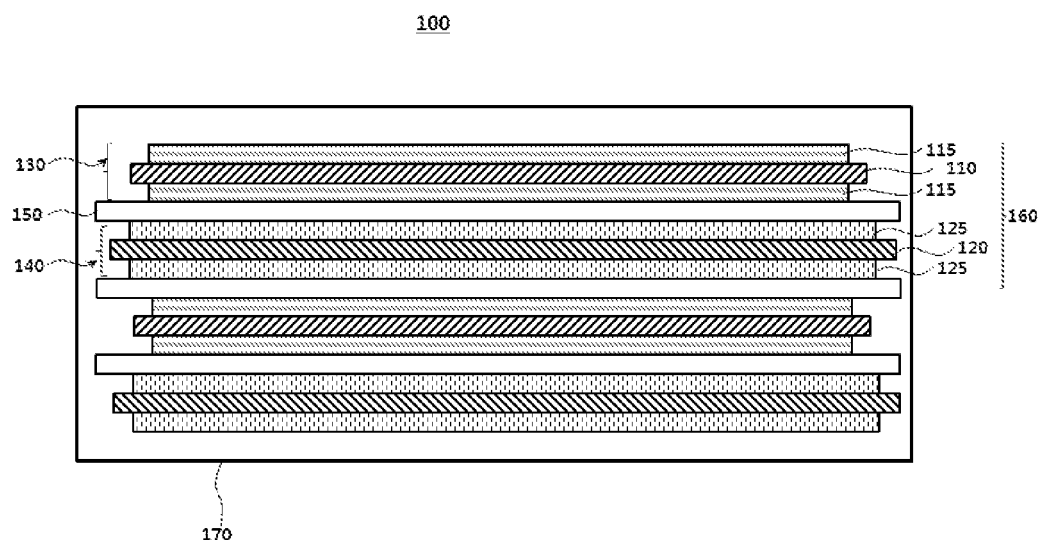

ELECTROLYTE FOR LITHIUM SECONDARY BATTERY AND LITHIUM SECONDARY BATTERY INCLUDING THE SAME

CROSS-REFERENCE TO RELATED APPLICATION

This application claims priority to Korean Patent Application No. 10-2020-0040945 filed Apr. 3, 2020, the disclosure of which is hereby incorporated by reference it its entirety.

BACKGROUND OF THE INVENTION

1. Field of the Invention

The present invention relates to an electrolyte for a lithium secondary battery and a lithium secondary battery including the same. More particularly, the present invention relates to an electrolyte for a lithium secondary battery including an organic solvent and a lithium secondary battery including the same.

2. Description of the Related Art

A secondary battery which can be charged and discharged repeatedly has been widely employed as a power source of a mobile electronic device such as a camcorder, a mobile phone, a laptop computer, etc., according to developments of information and display technologies. Recently, a battery pack including the secondary battery is being developed and applied as an eco-friendly power source of an electric automobile such as a hybrid vehicle.

The secondary battery includes, e.g., a lithium secondary battery, a nickel-cadmium battery, a nickel-hydrogen battery, etc. The lithium secondary battery is highlighted due to high operational voltage and energy density per unit weight, a high charging rate, a compact dimension, etc.

For example, the lithium secondary battery may include an electrode assembly including a cathode, an anode and a separation layer (separator), and an electrolyte immersing the electrode assembly. The lithium secondary battery may further include an outer case having, e.g., a pouch shape.

Recently, as an application of the lithium secondary battery is expanded, the lithium secondary battery having higher capacity and power has been developed. For example, materials for a cathode and an anode capable of providing higher capacity is being researched.

For example, a material that may replace a conventional carbon-based material is being researched. However, when the materials for the cathode and the anode are changed, an electrolyte contacting or reacting with the cathode and the anode is also required to be modified or newly designed.

For example, Korean Published Patent Application No. 10-2012-0101499 discloses a high voltage electrolyte for a lithium secondary battery.

SUMMARY OF THE INVENTION

According to an aspect of the present invention, there is provided an electrolyte for a lithium secondary battery providing improved chemical stability and operational reliability.

According to an aspect of the present invention, there is provided a lithium secondary battery including the electrolyte and providing improved chemical stability and operational reliability.

According to exemplary embodiments of the present invention, an electrolyte for a lithium secondary battery includes an organic solvent, a lithium salt, a first additive represented by Chemical Formula 1 and a second additive represented by Chemical Formula 2. Each amount of the first additive and the second additive is independently in a range from 0.01 wt % to 5 wt % based on a total weight of the electrolyte:

[Chemical Formula 1]

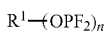

In Chemical Formula 1, $R^1$ is a saturated hydrocarbon backbone structure having 3 to 10 carbon atoms, and n is an integer of 1 to 3.

[Chemical Formula 2]

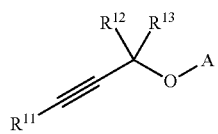

In Chemical Formula 2, $R^{11}$ to $R^{13}$ are each independently hydrogen, or a substituted or unsubstituted alkyl group having 1 to 6 carbon atoms, and A is a substituent represented by Chemical Formula 3 or Chemical Formula 4.

[Chemical Formula 3]

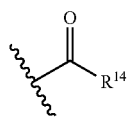

[Chemical Formula 4]

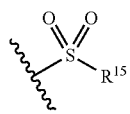

In Chemical Formulae 3 and 4, $R^{14}$ and $R^{15}$ are each independently a substituted or unsubstituted alkyl group having 1 to 6 carbon atoms, a substituted or unsubstituted aryl group having 6 to 12 carbon atoms, or $-OR^{16}$.

$R^{16}$ is a substituted or unsubstituted alkyl group having 1 to 6 carbon atoms, a substituted or unsubstituted aryl group having 6 to 12 carbon atoms, or an alkynyl group having 2 to 6 carbon atoms.

In some embodiments, in Chemical Formula 1, the saturated hydrocarbon backbone structure of $R^1$ may be linear.

In some embodiments, the first additive may include at least one of compounds represented by Chemical Formulae 1-1 to 1-3.

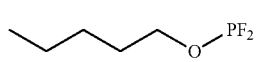

[Formula 1-1]

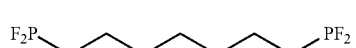

[Formula 1-2]

-continued

[Formula 1-3]

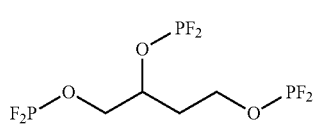

In some embodiments, the second additive may include a compound represented by Chemical Formula 4-1.

[Formula 4-1]

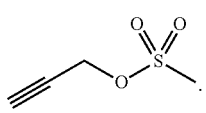

In some embodiments, an amount of the first additive may be in a range from 0.1 wt % to 3 wt % based on the total weight of the electrolyte.

In some embodiments, an amount of the first additive may be in a range from 0.1 wt % to 2 wt % based on the total weight of the electrolyte.

In some embodiments, an amount of the second additive may be in a range from 0.1 wt % to 3 wt % based on the total weight of the electrolyte.

In some embodiments, a weight ratio of the first additive and the second additive may be from 1:0.25 to 1:3.

In some embodiments, the organic solvent may include at least one selected from the group consisting of ethylene carbonate (EC), ethyl methyl carbonate (EMC), dimethyl carbonate (DMC), and diethyl carbonate (DEC).

In some embodiments, the lithium salt may include at least one of lithium hexafluorophosphate ($LiPF_6$) and lithium difluorophosphate ($LiPO_2F_2$).

In some embodiments, the electrolyte may further include a cyclic carbonate-based compound containing a double bond or a fluorine-substituted cyclic carbonate-based compound.

In some embodiments, the electrolyte may further include a sultone-based compound.

In some embodiments, the electrolyte may further include a cyclic sulfonate-based compound.

According to exemplary embodiments, a lithium secondary battery includes a cathode, an anode, a separation layer interposed between the cathode and the anode, and the electrolyte for a lithium secondary battery according to embodiments as described above.

In the electrolyte for a lithium secondary battery according to embodiments of the present invention, a first additive and a second additive may suppress a side reaction between an electrode and the electrolyte. For example, the first additive may passivate a metal of a cathode, and the second additive may form an electrically and thermally stable protective film on a surface of an anode. In this case, the side reaction between the electrode and the electrolyte may be suppressed, so that depletion of the electrolyte may be prevented. Additionally, an expansion of the battery due to a gas generation may be prevented.

Thus, life-span and capacity retention of the lithium secondary battery may be improved, and reliability and storage property at high temperature may be also improved.

BRIEF DESCRIPTION OF THE DRAWING

FIG. 1 is a schematic cross-sectional view illustrating a lithium secondary battery in accordance with exemplary embodiments.

DESCRIPTION OF THE INVENTION

According to exemplary embodiments of the present invention, an electrolyte for a lithium secondary battery including an organic solvent, a lithium salt and different first and second additives is provided. The additives may form a protective film to suppress an expansion of the lithium secondary battery and improve high-temperature storage properties. According to exemplary embodiments of the present invention, a lithium secondary battery including the electrolyte is provided.

Hereinafter, the present invention will be described in detail with reference to the accompanying drawings. However, those skilled in the art will appreciate that such embodiments described with reference to the accompanying drawings are provided to further understand the spirit of the present invention and do not limit subject matters to be protected as disclosed in the detailed description and appended claims.

Electrolyte for Lithium Secondary Battery

An electrolyte for a lithium secondary battery (hereinafter, that may be abbreviated as an electrolyte) according to embodiments of the present invention may include an organic solvent, a lithium salt mixed or dissolved in the organic solvent and two or more types of additives. For example, the electrolyte may be used as a non-aqueous electrolyte for a lithium secondary battery.

The organic solvent may include an organic compound that may provide a sufficient solubility to the lithium salt and the additives, and may not have a reactivity with the lithium secondary battery. In exemplary embodiments, the organic solvent may include a carbonate-based solvent, an ester-based solvent, an ether-based solvent, a ketone-based solvent, an alcohol-based solvent, an aprotic solvent, or the like. These may be used alone or in combination thereof.

Examples of the carbonate-based solvent may include dimethyl carbonate (DMC), ethyl methyl carbonate (EMC), methyl propyl carbonate, ethyl propyl carbonate, diethyl carbonate (DEC), dipropyl carbonate, propylene carbonate (PC), ethylene carbonate (EC), fluoroethylene carbonate (FEC), butylene carbonate, etc.

Examples of the ester-based solvent may include methyl acetate (MA), ethyl acetate (EA), n-propyl acetate (n-PA), 1,1-dimethylethyl acetate (DMEA), methyl propionate (MP), ethyl propionate (EP), gamma-butyrolacton (GBL), decanolide, valerolactone, mevalonolactone, caprolactone, etc.

Examples of the ether-based organic solvent may include dibutyl ether, tetraethylene glycol dimethyl ether (TEGDME), diethylene glycol dimethyl ether (DEGDME), dimethoxy ethane, 2-methyltetrahydrofuran, tetrahydrofuran, etc.

Cyclohexanone may be used as the ketone-based solvent. Examples of the alcohol-based solvent may include ethyl alcohol, isopropyl alcohol, etc.

The aprotic solvent may include a nitrile-based solvent, an amide-based solvent such as dimethyl formamide (DMF), a dioxolane-based solvent such as 1,3-dioxolane, a sulfolane-based solvent, etc.

In a preferable embodiment, the carbonate-based solvent may be used as the organic solvent. For example, the organic solvent may include ethylene carbonate (EC), ethyl methyl carbonate (EMC), dimethyl carbonate (DMC), diethyl carbonate (DEC), or a combination thereof. Preferably, a mixture of EC and EMC may be used as the organic solvent.

The lithium salt may include, e.g., a compound represented by $Li^+X^-$.

Non-limiting examples of the anion (X—) of the lithium salt may include $F^-$, $Cl^-$, $Br^-$, $I^-$, $NO_3^-$, $N(CN)_2^-$, $BF_4^-$, $ClO_4^-$, $PF_6^-$, $SbF_6^-$, $AsF_6^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, $(CF_3CF_2SO_2)_2N^-$, $PO_2F_2^-$, etc. These may be used alone or in a combination thereof.

Preferably, a mixture of lithium hexafluorophosphate ($LiPF_6$) and lithium difluorophosphate ($LiPO_2F_2$) may be used as the lithium salt. For example, $LiPO_2F_2$ may form a film having improved thermal stability on an electrode surface. $LiPF_6$ and $LiPO_2F_2$ may be mixed in a weight ratio of 1:0.5 to 1:2. Within the weight ratio range, the electrolyte may have enhanced ionic conductivity and electrode protection properties.

In an embodiment, the lithium salt may be included in a concentration from about 0.01 M to about 5 M, preferably from about 0.01 M to 2 M with respect to the organic solvent. Within the above range, a transfer of lithium ions and/or electrons may be promoted during charging and discharging of the lithium secondary battery, thereby providing improved capacity.

The first additive may be represented by the following Chemical Formula (1).

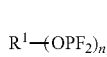
[Chemical Formula 1]

In the Chemical Formula 1 above, $R^1$ is a saturated hydrocarbon backbone structure having 3 to 10 carbon atoms, and n is an integer of 1 to 3.

The term "saturated hydrocarbon backbone structure" used herein may indicate a substituent derived from a hydrocarbon that does not contain an unsaturated bond. For example, the saturated hydrocarbon backbone structure may indicate a radical from which one or more hydrogen is removed from a saturated hydrocarbon, and may include an alkyl group and an alkylene group. The saturated hydrocarbon backbone structure may be linear, branched or cyclic.

Preferably, the saturated hydrocarbon backbone structure may be linear, so that a coordination bond with a metal element contained in a cathode or a chelating with the metal element may be effectively formed.

For example, as a lithium secondary battery is used, a metal (e.g., a transition metal) may be eluted from the cathode. The eluted metal may be electrodeposited on an anode, thereby deteriorating a performance of the anode. Additionally, when the lithium secondary battery is driven at a high voltage, a coating on the surface of the cathode may be decomposed to cause a side reaction between the surface of the cathode and the electrolyte.

The first additive may stabilize a structure of the cathode by coordinating with the metal of the cathode. In this case, when the lithium secondary battery is used and stored at a high temperature, the elution of the metal, a gas generation and an expansion of volume (thickness) may be suppressed. Accordingly, life-span and high-temperature storage properties of the lithium secondary battery may be improved.

Further, an increase of a resistance of the battery may be suppressed when being driven at a high voltage.

In exemplary embodiments, in Chemical Formula 1, when n is 1, $R^1$ may be an alkyl group having 3 to 10 carbon atoms. In this case, the first additive may include a compound represented by Chemical Formula 1-1 below.

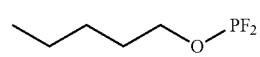
[Chemical Formula 1-1]

In exemplary embodiments, when n is 2, $R^1$ may be an alkylene group having 3 to 10 carbon atoms. In this case, the first additive may include a compound represented by Chemical Formula 1-2 below.

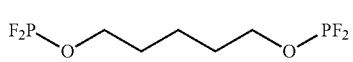
[Chemical Formula 1-2]

In exemplary embodiments, when n is 3, $R^1$ may be an alkylene group having 3 to 10 carbon atoms. In the alkylene group, a terminal end of the hydrocarbon backbone structure may be substituted with —$OPF_2$. Additionally, at least one —$OPF_2$ group may be bonded at an intermediate carbon atom of the hydrocarbon backbone structure. For example, when $R^1$ is a butylene group in which a secondary carbon atom is substituted with —$OPF_2$, the first additive may include a compound represented by Chemical Formula 1-3 below.

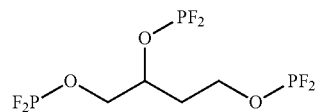
[Chemical Formula 1-3]

The first additive may be included in an amount from 0.01 to 5 weight percent (wt %) based on a total weight of the electrolyte. If the amount of the first additive is less than 0.01 wt %, the stabilizing effect of the cathode structure may be insufficient. If the amount of the first additive exceeds 5 wt %, an internal resistance of the lithium secondary battery may be excessively increased or the capacity of the lithium secondary battery may be decreased.

Preferably, the first additive may be included in an amount from 0.1 wt % to 2 wt %, more preferably from 0.3 wt % to 2 wt % or from 0.5 wt % to 2 wt %.

The second additive may be represented by Chemical Formula 2 below.

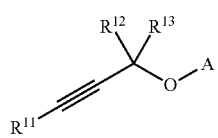
[Chemical Formula 2]

In the Chemical Formula 2 above, $R^{11}$ to $R^{13}$ are each independently hydrogen or a substituted or unsubstituted alkyl group having 1 to 6 carbon atoms.

A is a substituent represented by Chemical Formula 3 or Chemical Formula 4 below.

[Chemical Formula 3]

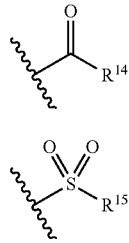

[Chemical Formula 4]

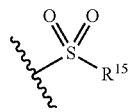

In the Chemical Formulae 3 and 4, $R^{14}$ and $R^{15}$ are each independently a substituted or unsubstituted alkyl group having 1 to 6 carbon atoms, a substituted or unsubstituted aryl group having 6 to 12 carbon atoms, or —$OR^{16}$.

$R^{16}$ is a substituted or unsubstituted alkyl group having 1 to 6 carbon atoms, a substituted or unsubstituted aryl group having 6 to 12 carbon atoms, or an alkynyl group having 2 to 6 carbon atoms.

For example, the second additive may include a compound represented by Formula 4-1 below.

[Chemical Formula 4-1]

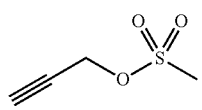

The second additive may form a coating or a film having excellent thermal stability on the electrode. For example, the second additive may form a complex with the eluted metal when the lithium secondary battery is operated. Accordingly, the eluted metal component may be removed from the electrolyte, so that side reactions caused by the metal component (e.g., a formation of dendrite of the eluted metal) may be suppressed. Additionally, the complex may be provided as the coating or the film to improve stability of the electrode.

The second additive may be included in an amount from 0.01 wt % to 5 wt % based on the total weight of the electrolyte. If the amount of the second additive is less than 0.01 wt %, the stabilizing effect of the anode structure may be insufficient. If the amount of the second additive exceeds 5 wt %, the internal resistance of the lithium secondary battery may be excessively increased or the capacity may be decreased.

Preferably, the second additive may be included in an amount from 0.1 wt % to 3 wt %, more preferably 0.3 wt % to 2 wt % or 0.5 wt % to 2 wt %.

In exemplary embodiments, a sum of the amounts of the first additive and the second additive may be from 0.5 wt % to 10 wt % based on the total weight of the electrolyte. Within the above-described range, the cathode and the anode of the battery may be effectively protected. Preferably, the sum of the amounts of the first additive and the second additive may be from 1 wt % to 10 wt %, or from 1 wt % to 5 wt % based on the total weight of the electrolyte.

In exemplary embodiments, the first additive and the second additive may be included in a weight ratio from 1:0.25 to 1:3. Within the weight ratio range, a cathode protection from the first additive and an anode protection from the second additive may be balanced. If the amount of the first additive is less than the above range, deterioration of the cathode may be accelerated relatively to the anode. If the amount the first additive exceeds the above range, deterioration of the anode may be accelerated relatively to the cathode.

Preferably, the weight ratio of the first additive and the second additive may be from 1:0.5 to 1:2, more preferably, from 1:0.5 to 1:1.

In exemplary embodiments, the electrolyte may include an additional additive such as a cyclic carbonate-based compound containing a double bond, a fluorine-substituted cyclic carbonate-based compound, a sultone-based compound, a cyclic sulfonate-based compound, or the like.

The cyclic carbonate-based compound containing the double bond may include vinylene carbonate, vinyl ethylene carbonate, or the like.

The fluorine-substituted cyclic carbonate-based compound may include fluoroethylene carbonate.

The cyclic carbonate-based compound containing the double bond and the fluorine-substituted cyclic carbonate-based compound may improve thermal and electrical durability of the film formed on the electrode surface.

For example, each of the cyclic carbonate-based compound containing the double bond and the fluorine-substituted cyclic carbonate-based compound may be included in an amount from 0.1 wt % to 5 wt % based on the total weight of the electrolyte. If the amount is less than 0.1 wt %, the durability of the film may be degraded. If the amount is more than 5 wt % by weight, a thickness of the film may be excessively increased. In this case, the resistance of the battery may increase to degrade a power of the battery.

The sultone-based compound may include 1,3-propane sultone, 1,3-propene sultone, 1,4-butane sultone, or the like.

The cyclic sulfonate-based compound may include 1,2-ethylene sulfate, 1,2-propylene sulfate, or the like.

The sultone-based compound and the cyclic sulfonate-based compound may form a more stable ion conductive film on the electrode surface. For example, the sultone-based compound and the cyclic sulfonate-based compound may form a structurally stable protective film on the electrode surface through a reaction with the second additive.

For example, each of the sultone-based compound and the cyclic sulfonate-based compound may be included in an amount from 0.1 wt % to 5 wt % based on the total weight of the electrolyte. If the amount is less than 0.1 wt %, the durability of the film may be degraded. If the amount is more than 5 wt %, the thickness of the film may be excessively increased. In this case, the resistance of the battery may increase to degrade the power of the battery.

Lithium Secondary Battery

FIG. 1 is a schematic cross-sectional view illustrating a lithium secondary battery in accordance with exemplary embodiments.

Referring to FIG. 1, a lithium secondary battery 100 may include an electrode assembly including a cathode 130, an anode 140 and a separation layer 150 interposed between the cathode and the anode. The electrode assembly may be accommodated in a case 170 together with the electrolyte according to the above-described exemplary embodiments to be impregnated therein.

The cathode 130 may include a cathode active material layer 115 formed by coating a cathode active material on a cathode current collector 110. The cathode active material may include a compound capable of reversibly intercalating and deintercalating lithium ions.

In exemplary embodiments, the cathode active material may include a lithium-transition metal oxide. For example, the lithium-transition metal oxide may include nickel (Ni), and may further include at least one of cobalt (Co) and manganese (Mn).

For example, the lithium-transition metal oxide may be represented by Chemical Formula 5 below.

$$Li_{1+a}Ni_{1-(x+y)}Co_xM_yO_2 \quad \text{[Chemical Formula 5]}$$

In the Chemical Formula 5 above, $-0.05 \leq a \leq 0.15$, $0.01 \leq x \leq 0.3$, $0.01 \leq y \leq 0.3$, and M may include at least one element selected from Mn, Mg, Sr, Ba, B, Al, Si, Ti, Zr and W.

A slurry may be prepared by mixing and stirring the cathode active material in a solvent with a binder, a conductive agent and/or a dispersive agent. The slurry may be coated on the cathode current collector 110, and then dried and pressed to form the cathode 130.

The cathode current collector 110 may include stainless-steel, nickel, aluminum, titanium, copper or an alloy thereof. Preferably, aluminum or an alloy thereof may be used.

The binder may include an organic based binder such as a polyvinylidene fluoride-hexafluoropropylene copolymer (PVDF-co-HFP), polyvinylidenefluoride (PVDF), polyacrylonitrile, polymethylmethacrylate, etc., or an aqueous based binder such as styrene-butadiene rubber (SBR) that may be used with a thickener such as carboxymethyl cellulose (CMC).

For example, a PVDF-based binder may be used as a cathode binder. In this case, an amount of the binder for forming the cathode active material layer may be reduced, and an amount of the cathode active material may be relatively increased. Thus, capacity and power of the lithium secondary battery may be further improved.

The conductive agent may be added to facilitate electron mobility between active material particles. For example, the conductive agent may include a carbon-based material such as graphite, carbon black, graphene, carbon nanotube, etc., and/or a metal-based material such as tin, tin oxide, titanium oxide, a perovskite material such as $LaSrCoO_3$ or $LaSrMnO_3$, etc.

The anode 140 may include an anode current collector 120 and an anode active material layer 125 formed by coating an anode active material on the anode current collector 120.

In exemplary embodiments, a silicon (Si)-based compound may be used as the anode active material. In some embodiments, silicon carbide (SiC) or a silicon-carbon particle including a carbon core and a silicon coating layer may be used as the anode active material.

The silicon-carbon particle may be formed by, e.g., depositing a silicon layer on a surface of a graphite core. In an embodiment, the silicon-carbon particle may be formed by coating the silicon layer on a commercially available graphite particle through a chemical vapor deposition (CVD) process using a silicon precursor compound such as a silane-based compound.

In some embodiments, the silicon-carbon particle may have a structure in which a plurality of carbon coating layers and silicon coating layers are alternately coated or stacked on the graphite core.

The anode current collector 120 may include gold, stainless-steel, nickel, aluminum, titanium, copper or an alloy thereof, preferably, may include copper or a copper alloy.

In some embodiments, the anode active material may be mixed and stirred together with a binder, a conductive agent and/or a dispersive additive in a solvent to form a slurry. The slurry may be coated on the anode current collector 120, and dried and pressed to obtain the anode 140. The conductive agent substantially the same as or similar to that as mentioned above may be used.

In some embodiments, the binder for the anode may include styrene-butadiene rubber (SBR) that may be reacted with the additives of the electrolyte as described above. In some embodiments, a thickener such as carboxymethyl cellulose (CMC) may be used together with SBR.

The separation layer 150 may be interposed between the cathode 130 and the anode 140. The separation layer 150 may include a porous polymer film prepared from, e.g., a polyolefin-based polymer such as an ethylene homopolymer, a propylene homopolymer, an ethylene/butene copolymer, an ethylene/hexene copolymer, an ethylene/methacrylate copolymer, or the like. The separation layer may also include a non-woven fabric formed from a glass fiber with a high melting point, a polyethylene terephthalate fiber, or the like.

In some embodiments, an area and/or a volume of the anode 140 (e.g., a contact area with the separation layer 150) may be greater than that of the cathode 130. Thus, lithium ions generated from the cathode 130 may be easily transferred to the anode 140 without a loss by, e.g., precipitation or sedimentation.

In exemplary embodiments, an electrode cell 160 may be defined by the cathode 130, the anode 140 and the separation layer 150, and a plurality of the electrode cells 160 may be stacked to form the electrode assembly having, e.g., a jelly roll shape. For example, the electrode assembly may be formed by winding, laminating or folding of the separation layer.

The electrode assembly may be accommodated in the case 170 together with the electrolyte according to exemplary embodiments to form the lithium secondary battery.

An electrode tab may be formed from each of the cathode current collector 110 and the anode current collector 120 to extend to one end of the case 170. The electrode tabs may be welded together with the one end of the case 170 to form electrode leads exposed at an outside of the case 170.

The lithium secondary battery may be fabricated into a cylindrical shape using a can, a prismatic shape, a pouch shape, a coin shape, etc.

Hereinafter, preferred embodiments are proposed to more concretely describe the present invention. However, the following examples are only given for illustrating the present invention and those skilled in the related art will obviously understand that various alterations and modifications are possible within the scope and spirit of the present invention. Such alterations and modifications are duly included in the appended claims.

EXAMPLES AND COMPARATIVE EXAMPLES (1) A slurry was prepared by mixing $Li[Ni_{0.8}Co_{0.1}Mn_{0.1}]O_2$ as a cathode active material, carbon black as a conductive material and polyvinylidene fluoride (PVdF) as a binder in a weight ratio of 96:2:2. The slurry was uniformly applied to an aluminum foil having a thickness of 15 μm, and vacuum-dried at 130° C. The dried slurry was pressed to prepare a cathode for a lithium secondary battery having a density of 3.667 g/cm³.

(2) A slurry including 97 wt % of an anode active material in which artificial graphite and natural graphite were mixed in a weight ratio of 7:3, 1 wt % of styrene-butadiene rubber (SBR) as a binder and 2 wt % of carboxymethyl cellulose (CMC) as a thickener was prepared. The anode slurry was uniformly coated, dried and pressed on a 15 μm-thick copper foil to prepare an anode having a density of 1.684 g/cm³.

(3) After dissolving 1 M LiPF$_6$ in a mixed solvent of EC/EMC (1:3; volume ratio), vinylene carbonate 0.5 wt %, fluoroethylene carbonate 1 wt %, LiPO$_2$F$_2$ 1 wt %, 1,3-propane sultone 0.5 wt %, 1,3-propene sultone 1 wt % and 1,2-ethylene sulfonate 0.5 wt % were mixed to prepare a base electrolyte.

The electrolytes of Examples and Comparative Examples were prepared by adding the additives shown in Table 1 to the base electrolyte.

(4) The cathode and the anode obtained as described above were notched with a proper size and stacked, and a separator (polyethylene, thickness: 20 μm) was interposed between the cathode and the anode to form an electrode cell. Each tab portion of the cathode and the anode was welded. The welded cathode/separator/anode assembly was inserted in a pouch, and three sides of the pouch except for an electrolyte injection side were sealed. The tab portions were also included in sealed portions. The electrolyte according to each Examples and Comparative Examples was injected through the electrolyte injection side, and then the electrolyte injection side was also sealed. Subsequently, the above structure was impregnated for more than 12 hours to prepare a lithium secondary battery with a capacity grade of about 2 Ah.

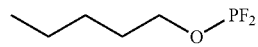

[Formula 1-1]

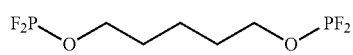

[Formula 1-2]

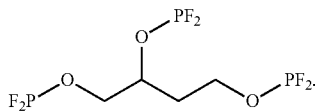

[Formula 1-3]

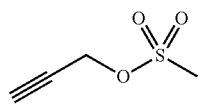

[Chemical Formula 4-1]

TABLE 1

| | First Additive | | Second Additive | | |
|---|---|---|---|---|---|
| | Type | Amount (wt % based on a total weight of the electrolyte) | Type | Amount (wt % based on a total weight of the electrolyte) | Weight Ratio of the first additive and the second additive |
| Example 1 | Chemical Formula 1-1 | 1.0 | Chemical Formula 4-1 | 1.0 | 1:1 |
| Example 2 | Chemical Formula 1-2 | 1.0 | Chemical Formula 4-1 | 1.0 | 1:1 |
| Example 3 | Chemical Formula 1-3 | 1.0 | Chemical Formula 4-1 | 1.0 | 1:1 |
| Example 4 | Chemical Formula 1-1 | 0.1 | Chemical Formula 4-1 | 0.1 | 1:1 |
| Example 5 | Chemical Formula 1-1 | 0.1 | Chemical Formula 4-1 | 1.0 | 1:10 |
| Example 6 | Chemical Formula 1-1 | 2.0 | Chemical Formula 4-1 | 1.0 | 2:1 |
| Example 7 | Chemical Formula 1-1 | 1.0 | Chemical Formula 4-1 | 0.1 | 10:1 |
| Example 8 | Chemical Formula 1-1 | 1.0 | Chemical Formula 4-1 | 2.0 | 1:2 |
| Example 9 | Chemical Formula 1-1 | 2.0 | Chemical Formula 4-1 | 2.0 | 1:1 |
| Example 10 | Chemical Formula 1-1 | 5.0 | Chemical Formula 4-1 | 5.0 | 1:1 |
| Comparative Example 1 | — | | | | |
| Comparative Example 2 | Chemical Formula 1-1 | 1.0 | — | | |
| Comparative Example 3 | Chemical Formula 1-1 | 1.0 | Chemical Formula 4-1 | 6.0 | 1:6 |
| Comparative Example 4 | — | | Chemical Formula 4-1 | 1.0 | — |
| Comparative Example 5 | Chemical Formula 1-1 | 6.0 | Chemical Formula 4-1 | 1.0 | 6:1 |

Experimental Example 1: Evaluation on Initial Capacity and Resistance

Charging (CC/CV ⅓C 4.2V 0.05 C CUT-OFF) and discharging (CC ⅓ C 2.5V CUT-OFF) of the electrolyte-injected secondary batteries of Examples and Comparative Examples were performed, and an initial discharge capacity of each battery was measured.

At a point where an SOC (State of Charge) of the battery was set to 60%, the C-rate sequentially increased or decreased to 0.2 C, 0.5 C, 1.0 C, 1.5 C, 2.0 C, 2.5 C and 3.0 C, and terminal points of a voltage were set as a linear equation when charging and discharging of the corresponding C-rate proceeded for 10 seconds. A slope of the linear equation was adopted as DCIR (direct current internal resistance).

Experimental Example 2: Evaluation of Gas Generation after Storage at High Temperature for 2 Weeks The secondary batteries injected with the electrolytes of Examples and Comparative Examples were left at 60° C. for 2 weeks, and then left at room temperature for 30 minutes. The batteries were placed in a chamber for measuring an amount of a gas generation. After forming a vacuum in the chamber, nitrogen gas was filled to form an atmospheric pressure, and a nitrogen volume ($V_0$) and a chamber internal pressure ($P_0$) were measured. After forming a vacuum at an inside of the chamber again, a hole was made in the battery, and a pressure at the inside of the chamber ($P_1$) was measured. The amount of the gas generation was calculated according to the following equation.

$$\text{Gas generation amount (mL)} = (V_0/P_0) * P_1$$

Experimental Example 3: Evaluation of Capacity and Resistance after 8 Weeks of Storage at High Temperature The secondary batteries injected with the electrolytes of Examples and Comparative Examples were stored for 8 weeks in a chamber at 60° C., and left at room temperature for 30 minutes.

Thereafter, DCIR of each battery was measured again by the method as described in Experimental Example 1.

After the DCIR measurement, a capacity measured when 1C rate CC discharge (2.7V cut-off) was performed was denominated by the initial discharge capacity to be represented as a percentage.

The evaluation results are shown in Table 2 below.

TABLE 2

| | Initial Property | | Gas Generation after High Temperature Storage for 2 weeks (ml) | Properties after High Temperature Storage for 8 weeks | | | |
|---|---|---|---|---|---|---|---|
| | Capacity (mAh) | DCIR (mΩ) | | Capacity (mAh) | Capacity Retention (%) | DCIR (mΩ) | Increased Ratio of DCIR (%) |
| Example 1 | 2044 | 39.91 | 8.1 | 1739 | 85 | 57.97 | 145 |
| Example 2 | 2035 | 41.21 | 9.3 | 1711 | 84 | 60.27 | 146 |
| Example 3 | 2023 | 42.11 | 10.3 | 1680 | 83 | 62.17 | 148 |
| Example 4 | 2066 | 41.14 | 15.2 | 1570 | 76 | 65.11 | 158 |
| Example 5 | 2023 | 43.81 | 13.4 | 1618 | 80 | 67.47 | 154 |
| Example 6 | 2020 | 42.71 | 11.0 | 1686 | 83 | 63.47 | 149 |
| Example 7 | 2030 | 42.56 | 14.3 | 1604 | 79 | 65.12 | 153 |
| Example 8 | 2011 | 44.61 | 10.7 | 1669 | 83 | 66.02 | 148 |
| Example 9 | 2016 | 45.51 | 10.5 | 1653 | 82 | 67.81 | 149 |
| Example 10 | 2031 | 42.03 | 12.4 | 1645 | 81 | 63.47 | 151 |
| Comparative Example 1 | 2069 | 41.34 | 20.2 | 1345 | 65 | 69.45 | 168 |
| Comparative Example 2 | 2056 | 37.5 | 17.5 | 1480 | 72 | 65.25 | 174 |
| Comparative Example 3 | 2011 | 46.91 | 16.7 | 1488 | 74 | 78.81 | 168 |
| Comparative Example 4 | 2053 | 43.91 | 18.3 | 1458 | 71 | 72.45 | 165 |
| Comparative Example 5 | 2018 | 45.31 | 16.9 | 1453 | 72 | 75.67 | 167 |

Referring to Table 2, in the batteries of Examples where the first additive and the second additive were used, the volume expansion and the increase of the internal resistance were suppressed while increasing the capacity retention relatively to those in the batteries of Comparative Examples.

What is claimed is:

1. An electrolyte for a lithium secondary battery, comprising:
   an organic solvent;
   a lithium salt;
   a first additive represented by Chemical Formula 1; and
   a second additive represented by Chemical Formula 2,
   wherein each amount of the first additive and the second additive is independently in a range from 0.01 wt % to 5 wt % based on a total weight of the electrolyte:

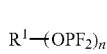

[Chemical Formula 1]

wherein, in Chemical Formula 1, $R^1$ is a saturated hydrocarbon backbone structure having 3 to 10 carbon atoms, and n is an integer of 1 to 3,

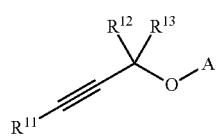

[Chemical Formula 2]

wherein, in Chemical Formula 2, $R^{11}$ to $R^{13}$ are each independently hydrogen, or a substituted or unsubstituted alkyl group having 1 to 6 carbon atoms, and A is a substituent represented by Chemical Formula 3 or Chemical Formula 4,

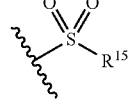

[Chemical Formula 3]

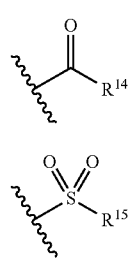

[Chemical Formula 4]

wherein, in Chemical Formulae 3 and 4, $R^{14}$ and $R^{15}$ are each independently a substituted or unsubstituted alkyl group having 1 to 6 carbon atoms, a substituted or unsubstituted aryl group having 6 to 12 carbon atoms, or —$OR^{16}$, and
$R^{16}$ is a substituted or unsubstituted alkyl group having 1 to 6 carbon atoms, a substituted or unsubstituted aryl group having 6 to 12 carbon atoms, or an alkynyl group having 2 to 6 carbon atoms.

2. The electrolyte for a lithium secondary battery according to claim 1, wherein, in Chemical Formula 1, the saturated hydrocarbon backbone structure of $R^1$ is linear.

3. The electrolyte for a lithium secondary battery according to claim 1, wherein the first additive includes at least one of compounds represented by Chemical Formulae 1-1 to 1-3:

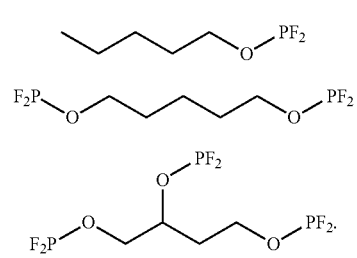

[Formula 1-1]

[Formula 1-2]

[Formula 1-3]

4. The electrolyte for a lithium secondary battery according to claim 1, wherein the second additive includes a compound represented by Chemical Formula 4-1:

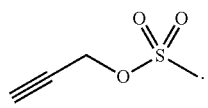

[Formula 4-1]

5. The electrolyte for a lithium secondary battery according to claim 1, wherein an amount of the first additive is in a range from 0.1 wt % to 3 wt % based on the total weight of the electrolyte.

6. The electrolyte for a lithium secondary battery according to claim 1, wherein an amount of the first additive is in a range from 0.1 wt % to 2 wt % based on the total weight of the electrolyte.

7. The electrolyte for a lithium secondary battery according to claim 1, wherein an amount of the second additive is in a range from 0.1 wt % to 3 wt % based on the total weight of the electrolyte.

8. The electrolyte for a lithium secondary battery according to claim 1, wherein a weight ratio of the first additive and the second additive is from 1:0.25 to 1:3.

9. The electrolyte for a lithium secondary battery according to claim 1, wherein the organic solvent includes at least one selected from the group consisting of ethylene carbonate (EC), ethyl methyl carbonate (EMC), dimethyl carbonate (DMC), and diethyl carbonate (DEC).

10. The electrolyte for a lithium secondary battery according to claim 1, wherein the lithium salt includes at least one of lithium hexafluorophosphate ($LiPF_6$) and lithium difluorophosphate ($LiPO_2F_2$).

11. The electrolyte for a lithium secondary battery according to claim 1, further comprising a cyclic carbonate-based compound containing a double bond or a fluorine-substituted cyclic carbonate-based compound.

12. The electrolyte for a lithium secondary battery according to claim 1, further comprising a sultone-based compound.

13. The electrolyte for a lithium secondary battery according to claim 1, further comprising a cyclic sulfonate-based compound.

14. A lithium secondary battery, comprising:
   a cathode;
   an anode;
   a separation layer interposed between the cathode and the anode; and
   the electrolyte for a lithium secondary battery according to claim 1.

* * * * *